United States Patent [19]
Hudson

[11] Patent Number: 5,825,028
[45] Date of Patent: *Oct. 20, 1998

[54] QUALITY CONTROL METHOD FOR DETECTING DEFECTIVE POLISHING PADS USED IN PLANARIZATION OF SEMICONDUCTOR WAFERS

[75] Inventor: Guy F. Hudson, Boise, Id.

[73] Assignee: Micron Technology, Inc., Boise, Id.

[*] Notice: The term of this patent shall not extend beyond the expiration date of Pat. No. 5,650,619.

[21] Appl. No.: 833,917

[22] Filed: Apr. 10, 1997

Related U.S. Application Data

[63] Continuation of Ser. No. 576,781, Dec. 21, 1995, Pat. No. 5,650,619.
[51] Int. Cl.⁶ .................................................. G01T 1/161
[52] U.S. Cl. ............................................................ 250/302
[58] Field of Search ................................ 250/302, 458.1

[56] References Cited

U.S. PATENT DOCUMENTS 2,806,959  9/1957  Forest et al. ............................ 250/302

*Primary Examiner*—Bruce Anderson
*Attorney, Agent, or Firm*—Seed and Berry LLP

[57] ABSTRACT

The present invention is a quality control method that denotes non-uniformities of structural features on a planarizing surface of a polishing pad across substantially the whole surface area of the pad. In one embodiment of the method, an indicating compound applied to the planarizing surface of a polishing pad adjoins to the structural feature on the planarizing surface of the pad in proportion to the density of the structural feature. Excess indicating compound is then removed from the planarizing surface of the pad to leave the portion of the indicating compound that adjoined to the structural feature in the pad. The indicating compound is readily visible, and thus non-uniform areas on the planarizing surface with a high density of the structural feature are stained a darker shade of color than other areas on the pad. The planarizing surface is subsequently evaluated to determine whether the surface area with an excess density of indicating compound is within a desired range.

36 Claims, 3 Drawing Sheets

QUALITY CONTROL METHOD FOR DETECTING DEFECTIVE POLISHING PADS USED IN PLANARIZATION OF SEMICONDUCTOR WAFERS

CROSS-REFERENCE TO RELATED APPLICATION

This application is a continuation of U.S. patent application Ser. No. 08/576,781, filed Dec. 21, 1995 U.S. Pat. No. 5,650,619.

TECHNICAL FIELD

The present invention relates to a quality control method for detecting defective polishing pads used in chemical-mechanical planarization of semiconductor wafers. More specifically, the present invention is a method that denotes non-uniformities of a structural characteristic of polishing pads.

BACKGROUND OF THE INVENTION

Chemical-mechanical planarization ("CMP") processes create planar surfaces in the fabrication of multi-level interconnect and ultra-high density integrated circuits. In a typical CMP process, a wafer engages a polishing pad in the presence of a slurry under controlled chemical, pressure, velocity, and temperature conditions. At least one of the wafer or polishing pad moves with respect to the other to pass the surface of the wafer over the surface of the pad. Slurry solutions generally contain small, abrasive particles of silica or alumina that mechanically remove the surface of the wafer, and chemicals that chemically remove the surface of the wafer.

CMP processes must create a uniformly planar surface on a wafer at a desired endpoint so that the geometries of the component parts of a die may be accurately positioned across the full surface of the wafer. The uniformity of the planarized surface is a function of several factors, one of which is the rate at which the thickness of the wafer decreases as it is planarized (the "polishing rate"). An excessively high polishing rate, for example, is difficult to control and often decreases the uniformity of the planar surface. Thus, in order to create a sufficiently uniform surface, it is important to control the polishing rate of the CMP process.

CMP processes must also create such uniform wafer surfaces quickly to maximize the throughput of finished microelectronic devices. The throughput of CMP processes is a function of several factors including the polishing rate of the wafer and the ability to accurately stop the CMP process at a desired endpoint. A reasonably high polishing rate generally results in a greater throughput because it requires less time to planarize a wafer. Accurately stopping the CMP process at a desired endpoint is also important to maintaining a high throughput because the thickness of the dielectric layer must be within an acceptable range; if the thickness of the dielectric layer is not within an acceptable range, the wafer must be re-planarized until it reaches a desired endpoint. Such re-planarization of a wafer significantly reduces the throughput of current CMP processes. In practice, endpoints are estimated by measuring the planarizing time to planarize the first wafer in a run to the actual desired endpoint, and then planarizing the rest of the wafers in the run for a similar period of time. Thus, it is important to control the polishing rate to provide a consistent polishing rate from one wafer to the next.

One problem with current CMP processes is that the polishing rate varies over a large number of wafers because certain structural features on the planarizing surface of the pad vary over the life of a pad. One such structural feature is the uniformity of the distribution of filler material throughout the pad. Polishing pads can be made from a mixture of a continuous phase polymer material and a filler material. The filler material, however, may agglomerate before the mixture cures, resulting in a non-uniform distribution of the filler material in the continuous phase material. Consequently, regions on the planarizing surface of a pad with excess filler material may have a high or low polishing rate, depending upon the nature of the filler material, while regions that lack filler material have a conversely low or high polishing rate. Although many efforts have been made to distribute the filler material throughout the continuous phase material homogeneously, many pads still have a non-uniform distribution of filler material on their planarizing surface. Moreover, the non-uniform areas of the filler material are not visibly distinguishable from other areas on the pad. Accordingly, it would be desirable to determine the extent of the non-uniform areas of filler material and other structural features on the planarizing surface of a pad to determine whether the pad is acceptable.

Conventional processes for determining the structural features on the planarizing surface of a polishing pad include Shore Hardness testing and Scanning Electron Microscope (SEM) testing. In Shore Hardness testing, a machine measures the hardness of the planarizing surface at a few random points across the pad. Similarly, in SEM testing, an electron microscope photographs a few random points on the pad. One problem with Shore Hardness and SEM testing is that they only analyze a small percentage of the surface area of the planarizing surface because it takes too long to test the whole surface area of the pad. Many non-uniformities of a structural feature, therefore, are not detected by Shore Hardness or SEM testing techniques. Thus, it would be desirable to develop a process for denoting non-uniformities of selected structural features on the planarizing surface on a macro-level across the whole surface of the polishing pad.

SUMMARY OF THE INVENTION

The inventive quality control method denotes non-uniformities of structural features on a planarizing surface of a polishing pad across substantially the whole surface area of the pad. In one embodiment of the method, an indicating compound applied to the planarizing surface of a polishing pad adjoins to the structural feature in proportion to the density of the structural feature at the planarizing surface. Excess indicating compound is then removed from the planarizing surface of the pad to leave only the adjoined portion of the indicating compound on the pad. The indicating compound is readily visible and thus non-uniform areas on the planarizing surface with a high density of the structural feature are stained a darker shade of color than other areas on the pad. The planarizing surface is subsequently evaluated to determine whether the surface area with an excess density of indicating compound is within a desired range.

DETAILED DESCRIPTION OF THE INVENTION

The present invention provides a quality control method that denotes the uniformity of a structural feature on a planarizing surface of a polishing pad. Unlike conventional Shore Hardness and SEM testing techniques that only measure the structural feature at a few points on the planarizing surface, the inventive process denotes the uniformity of the structural feature across substantially the whole surface of the pad. The invention stains the pad with a readily visible indicating compound that adjoins to the structural feature in proportion to the density of the structural feature. Various embodiments of the method of the invention are described in greater detail below in FIGS. 1–6, in which like reference numbers refer to like parts throughout the various figures.

Figure 1:
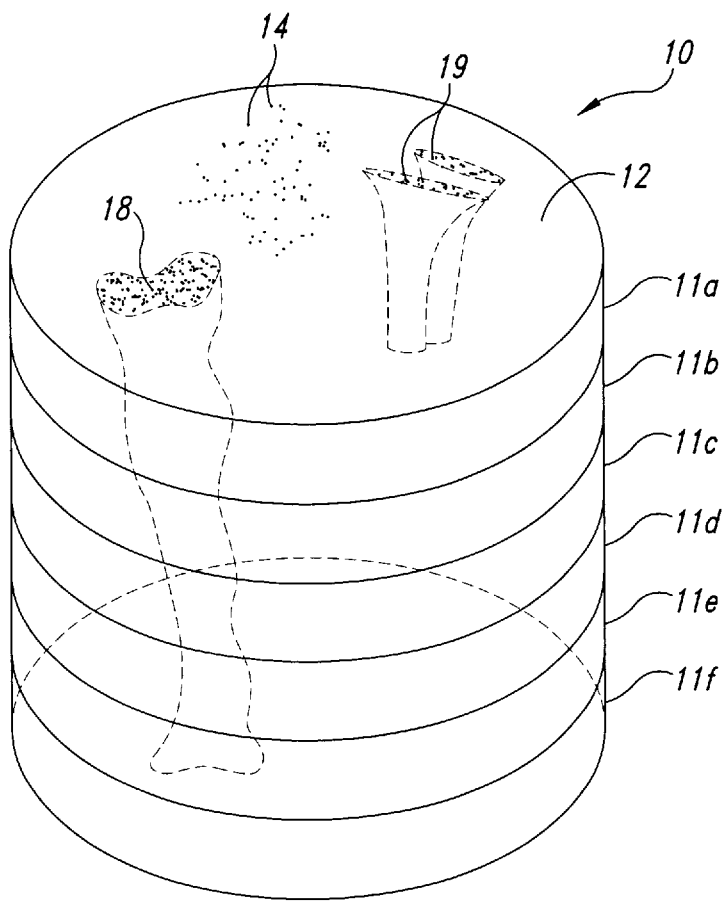
FIG. 1 is an isometric view of a cake of polishing pad material.

FIG. 1 illustrates a cake of pad material 10 from which a number of individual polishing pads 11(a)–11(f) are cut. The cake 10 is made from a mixture of a continuous phase material 12 and an abrasive filler material 14 that is cured into a large, solid cake of pad material. The continuous phase material 12 is typically polyurethane, and the filler material 14 is generally small, hollow particles. The filler material 14 initially mixes uniformly with the continuous phase material, but then it agglomerates into clusters of random shapes 18 as the cake 10 cures. The clusters 18 of filler material 14 form high density regions of filler material 14 throughout the cake 10. The clusters 18 of filler material 14 are not readily visible without the process of the present invention, and thus they are shown in phantom in FIGS. 1–2B. After the cake 10 cures, the pads 11(a)–11(f) are cut apart from one another.

Figure 2A:
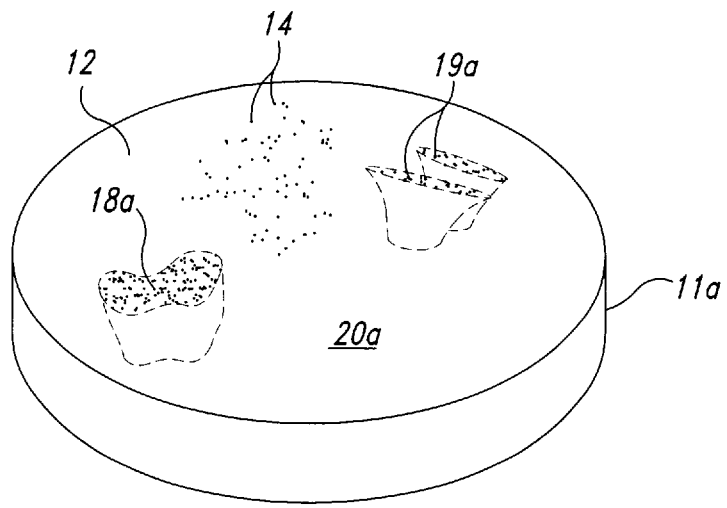
FIG. 2A is an isometric view of a polishing pad cut from the cake of pad material of FIG. 1.

FIG. 2A illustrates pad 11(a) after it has been cut from the cake 10 of pad material. The filler material 14 forms a large non-uniform area 18(a) and several small non-uniform areas 19(a) on the pad's planarizing surface 20(a). As with the clusters 18 of filler material 14, the non-uniform areas 18(a) and 19(a) are shown in phantom in FIGS. 2A and 2B because they are not readily visible without the process of the present invention. The non-uniform areas 18(a) and 19(a) of filler material 14 may be any size or shape depending upon the cross-sectional shape of the cluster of filler material 14 at the planarizing surface. The size and shape of the non-uniform areas also varies throughout the depth of the pad, as best shown by the small non-uniform areas 19(a). Since a thin layer of pad material is removed from the pad each time the pad is conditioned, the size and shape of the non-uniform areas 18(a) and 19(a) on the planarizing surface 20(a) of pad 11(a) vary over the life of pad 11(a). Thus, the polishing rate of a pad also varies over the life of the pad.

Figure 2B:
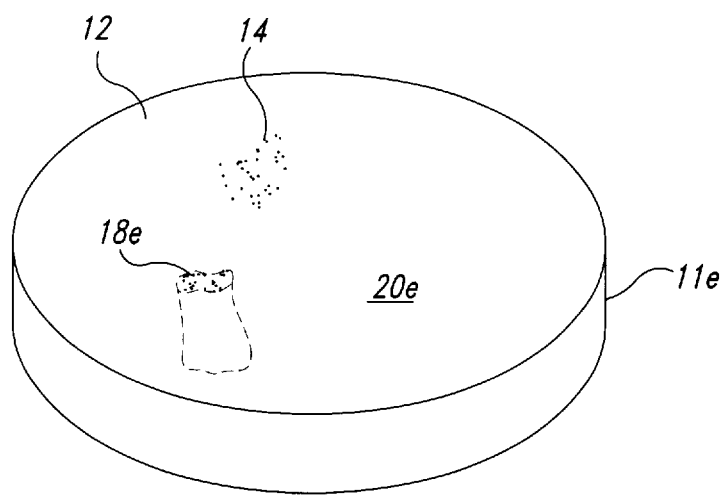
FIG. 2B is an isometric view of another polishing pad cut from the cake of pad material of FIG. 1.

FIG. 2B illustrates pad 11(e) after it has been cut from the cake 10 of pad material. In pad 11(e), the filler material 14 forms a mid-sized non-uniform area 18(e) on its planarizing surface 20(e), but none of the small non-uniform regions 19 exist on pad 11(e) because they do not extend to the level of pad 11(e) in the cake 10 of pad material. The non-uniform area 18(e) on pad 11(e) is formed from the same cluster 18 of filler material 14 as the non-uniform area 18(a) on pad 11(a). Thus, the uniformity of the filler material 14 also varies from one pad to another.

Figure 3:
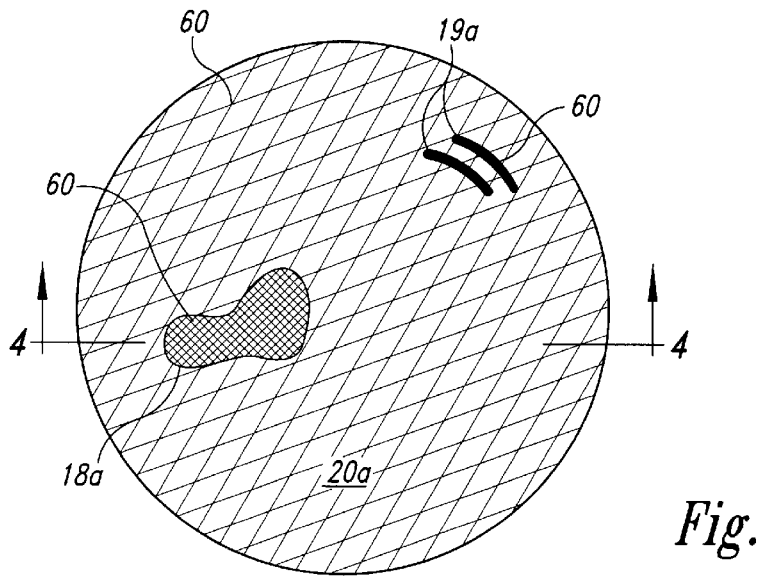
FIG. 3 is a top elevational view of a polishing pad upon which an indicating compound has been applied in accordance with the invention.

FIG. 3 illustrates the polishing pad 11(a) after the non-uniform areas 18(a) and 19(a) are denoted according to the invention. An indicating compound 60 applied to the planarizing surface 20(a) of the pad 11(a) makes the non-uniform areas 18(a) and 19(a) easily visible across the whole planarizing surface 20(a). The indicating compound 60 is a visible stain that adjoins to either the continuous phase material 12 or the filler material 14. The indicating compound 60 accordingly stains the planarizing surface 20(a), denoting the density of the filler material 14 throughout the continuous phase material 12. The indicating compound 60 preferably stains areas with high densities of filler material 14 a darker, more intense shade of color than the areas with normal concentrations of filler material 14.

Figure 4:
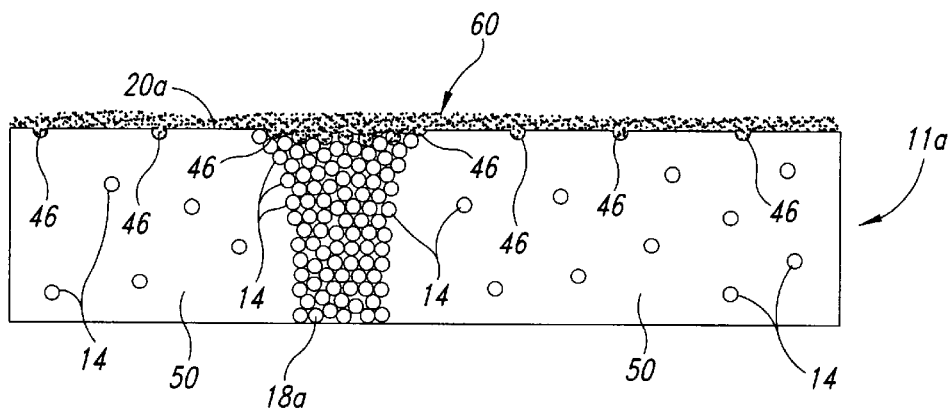
FIG. 4 is a partial cross-sectional view of the pad of FIG. 3.
Figure 5:
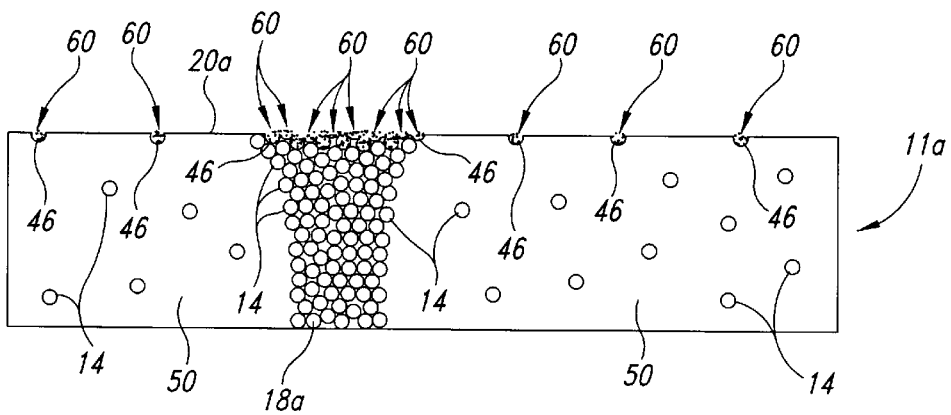
FIG. 5 is another partial cross-sectional view of the pad of FIG. 3.

FIGS. 4 and 5 illustrate the operation of the method of the invention. Referring to FIG. 4, the filler material 14 is made from small, hollow particles that form a number of porous cavities 46 in the planarizing surface 20(a) when the pad 11(a) is cut or conditioned. The filler material 46 may also be made from other materials, such as solid abrasive particles. The top surface of the non-uniform area 18(a), which has a high density of filler material 14 and porous cavities 46, is thus more porous than the adjacent regions 50. The indicating compound 60 is applied to the planarizing surface 20(a) of the pad 11(a) so that it covers the planarizing surface 20(a) and adjoins to the porous cavities 46. Referring to FIG. 5, the excess indicating compound 60 is removed from the planarizing surface 20(a), leaving the adjoined indicating compound 60 in the porous cavities 46 on the planarizing surface 20(a). Because the porosity of the non-uniform area 18(a) is higher than that of the adjacent regions 50, the remaining indicating compound 60 on the planarizing surface 20(a) stains the non-uniform area 18(a) a darker, more intense shade of color than the adjacent regions 50, as also shown in FIG. 3. In a preferred embodiment, the indicating compound 60 is applied to the planarizing surface 20(a) of the pad 11(a), and pressure is applied to the indicating compound 60. Under pressure, more indicating compound 60 penetrates into the porous cavities formed from the small, hollow spheres of filler material 14 to enhance the contrast between non-uniform areas and adjacent regions.

The indicating compound 60 is preferably an oxidant, such as potassium iodate or ferric nitrate, that is added to the slurry and deposited onto the polishing pad while wafers with metal features or metal films (not shown) are planarized. When the indicating compound is an oxidant, it is initially transparent and then it reduces and changes to an opaque color upon contact with the wafer. The pressure between the wafer and the polishing pad also forces the indicating compound into the pores created by the filler material to better differentiate the non-uniform areas on the planarizing surface, as discussed above. Other types of indicating compounds within the scope of the invention include fluorescent materials that are readily visible under ultraviolet light.

The present invention is not limited to detecting non-uniform areas of filler material across the surface of the pad, as other structural features on the planarizing surface of the pad may be detected using the method of the invention. One other structural feature of the pad that can be detected using the present invention is the non-uniform reaction of the polymers in the continuous phase material. Some of the polymers in the continuous phase material do not react, and thus there are non-uniform regions within the continuous phase material itself. By covering the planarizing surface with an indicating compound that adjoins to the unreacted polymers, the non-uniformities in the structural characteristic of the polishing pad may be denoted and evaluated.

Another important aspect of the invention is to evaluate the percentage of surface area on the planarizing surface of the polishing pad denoted by a high density of indicating compound. As best shown in FIG. 3, the non-uniform areas 18(*a*) and 19(*a*) have a high density of indicating compound 60. In general, if more than five percent of the surface area of the polishing pad is denoted by a high density of the indicating compound, then the polishing rate of the pad will be difficult to control. Also, if the density of indicating compound is extremely high in even a small area on the planarizing surface, such as non-uniform areas 19(*a*), then the pad will likely produce non-uniform wafer surfaces because the portions of the wafer passing over areas 19(*a*) will be planarized at a significantly different polishing rate than other portions of the wafer. Therefore, in order to determine the quality of a given pad, it is necessary to evaluate the amount of surface area denoted by the indicating compound and the density of the compound at those areas.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. In planarization of wafer, a method for evaluating structural characteristics of a planarizing surface of a polishing pad having filler material distributed in a continuous phase material, comprising:

staining the planarizing surface of the pad with an indicating compound that contrasts the filler material from the continuous phase material;

denoting a distribution of stain across the planarizing surface of the polishing pad.

2. The method of claim 1 wherein the act of staining comprises:

applying the indicating compound to the planarizing surface of the pad; and removing a substantial portion of the indicating compound from the planarizing surface.

3. The method of claim 2 wherein the act of staining the planarizing surface further comprises pressing the indicating compound into the planarizing surface prior to the removing step.

4. The method of claim 2 wherein the act of applying comprises depositing the indicating compound onto the planarizing surface along with a planarizing solution.

5. The method of claim 4 wherein the indicating compound comprises potassium iodate and the applying step comprises adding the potassium iodate to the planarizing solution during chemical-mechanical planarization.

6. The method of claim 4 wherein the indicating compound comprises ferric nitrate and the applying step comprises adding the ferric nitrate to the planarizing solution during chemical-mechanical planarization.

7. The method of claim 4 wherein the indicating compound comprises a fluorescent material and the applying step comprises adding the fluorescent material to the planarizing solution during chemical-mechanical planarization.

8. The method of claim 1 wherein act of denoting the distribution of stain comprises visually sensing color differences corresponding to concentrations of the indicating compound across the planarizing surface.

9. A method for evaluating non-uniformities of a planarizing surface of a wafer polishing pad having a distribution of a structural material in a continuous phase material, comprising:

staining a planarizing surface of the pad with an indicating compound that preferentially adjoins to one of the structural material and the continuous phase material;

denoting a distribution of indicating compound across the planarizing surface of the polishing pad to determine a distribution of the structural material relative to the continuous phase material across the planarizing surface.

10. The method of claim 9 wherein the structural material comprises a filler material that forms porous structures in the continuous phase matrix material, and wherein the staining step comprises depositing the indicating compound in a liquid medium that at least partially fills a portion of the porous structures at the planarizing surface.

11. The method of claim 9 wherein the indicating compound is potassium iodate and the liquid medium is a planarizing solution, and wherein the applying step comprises dispensing the planarizing solution on the polishing pad during planarization of a wafer.

12. The method of claim 9 wherein the indicating compound is ferric nitrate and the liquid medium is a planarizing solution, and wherein the applying step comprises dispensing the planarizing solution on the polishing pad during planarization of a wafer.

13. The method of claim 9 wherein the indicating compound is a fluorescent dye and the liquid medium is a planarizing solution, and wherein the applying step comprises dispensing the planarizing solution on the polishing pad during planarization of a wafer.

14. A method for evaluating structural characteristics of a planarizing surface of a polishing pad having a filler material distributed in a continuous phase material, comprising:

depositing a planarizing solution having potassium iodate onto the polishing pad during planarization of a wafer with exposed metal features, the potassium iodate collecting in pores formed by the filler material;

denoting a distribution of potassium iodate across the planarizing surface of the polishing pad to determine a distribution of the filler material relative to the continuous phase material across the planarizing surface.

15. The method of claim 14 wherein the act of denoting comprises visually sensing color differences corresponding to different concentrations of potassium iodate across the planarizing surface.

16. A method for evaluating structural characteristics of a planarizing surface of a polishing pad having a filler material in a continuous phase material, comprising:

depositing a planarizing solution having ferric nitrate onto the polishing pad during planarization of a wafer with exposed metal features, the ferric nitrate collecting in pores formed by the filler material;

denoting a distribution of ferric nitrate across the planarizing surface of the polishing pad to determine a distribution of the filler material relative to the continuous phase material across the planarizing surface.

17. The method of claim 16 wherein the act of denoting comprises visually sensing color differences corresponding to different concentrations of ferric nitrate across the planarizing surface.

18. A method for evaluating structural characteristics of a planarizing surface of a wafer polishing pad having a filler material distributed in a continuous phase material, comprising:

depositing a planarizing solution having a fluorescent dye onto the polishing pad during planarization of a wafer, the fluorescent dye collecting in pores formed by the filler material;

denoting a distribution of the fluorescent dye across the planarizing surface of the polishing pad to determine a distribution of the filler material relative to the continuous phase material across the planarizing surface.

19. The method of claim 18 wherein the act of denoting comprises visually sensing color differences corresponding to different concentrations of the fluorescent dye across the planarizing surface.

20. In planarization of a wafer on a polishing pad having a filler material distributed in a continuous phase material, a method of evaluating structural characteristics of a planarizing surface of the polishing pad, comprising:

staining the planarizing surface of the polishing pad with an indicating compound that preferentially remains with one of the filler material and the continuous phase material; and detecting a distribution of the indicating compound across the surface of the polishing pad to determine a corresponding distribution of the preferred one of the filler material and the continuous phase material.

21. The method of claim 20 wherein the act of staining comprises:

applying the indicating compound to the planarizing surface of the pad; and, removing a portion of the indicating compound from the planarizing surface of the pad.

22. The method of claim 21 wherein the pressing step occurs prior to the removing step.

23. The method of claim 21 wherein the pressing step occurs during planarization of a wafer.

24. The method of claim 20 wherein the act of staining comprises pressing the indicating compound into the planarizing surface.

25. A method of evaluating a surface characteristic of a planarizing surface of a polishing pad having a continuous phase material and a filler material distributed in the continuous phase material, comprising:

depositing an indicating compound that preferentially adjoins to one of the filler material and the continuous phase material;

pressing the indicating compound against the planarizing surface; and detecting a distribution of the indicating compound across the surface of the polishing pad to determine a corresponding distribution of the one of the filler material and the continuous phase material to which the indicating compound preferentially adjoins.

26. The method of claim 25 wherein the act of depositing the indicating compound onto the planarizing surface comprises dispensing a planarizing solution with the indicating compound onto the planarizing surface of the polishing pad.

27. The method of claim 25 wherein the act of pressing the indicating compound against the planarizing surface comprises engaging a wafer with the polishing pad and planarizing the wafer while the indicating compound is on the planarizing surface.

28. The method of claim 25 wherein:

the act of depositing the indicating compound onto the planarizing surface comprises dispensing a planarizing solution with the indicating compound onto the planarizing surface of the polishing pad; and the act of pressing the indicating compound against the planarizing surface comprises engaging a wafer with the polishing pad and planarizing the wafer while the indicating compound is on the planarizing surface.

29. The method of claim 28 wherein the indicating compound comprises potassium iodate and the act of dispensing the indicating compound with the planarizing solution comprises adding the potassium iodate to the planarizing solution.

30. The method of claim 28 wherein the indicating compound comprises ferric nitrate and the act of dispensing the indicating compound with the planarizing solution comprises adding the ferric nitrate to the planarizing solution.

31. The method of claim 28 wherein the indicating compound comprises a fluorescent material and the act of dispensing the indicating compound with the planarizing solution comprises adding the fluorescent material to the planarizing solution.

32. A method of planarizing a wafer on a polishing pad having a continuous phase material and a filler material distributed in the continuous phase material, comprising:

engaging the wafer with a planarizing surface of the polishing pad;

moving at least one of the wafer or the polishing pad with respect to the other to remove material from the wafer;

depositing an indicating compound onto the polishing pad during the act of moving that preferentially adjoins to one of the filler material and the continuous phase material; and detecting a distribution of the indicating compound across the surface of the polishing pad to determine a corresponding distribution of the one of the filler material and the continuous phase material to which the indicating compound preferentially adjoins.

33. The method of claim 32 wherein the act of depositing the indicating compound onto the planarizing surface comprises dispensing the a planarizing solution with the indicating compound onto the planarizing surface of the polishing pad.

34. The method of claim 33 wherein the indicating compound comprises potassium iodate and the act of dispensing the indicating compound with the planarizing solution comprises adding the potassium iodate to the planarizing solution.

35. The method of claim 33 wherein the indicating compound comprises ferric nitrate and the act of dispensing the indicating compound with the planarizing solution comprises adding the ferric nitrate to the planarizing solution.

36. The method of claim 33 wherein the indicating compound comprises a fluorescent material and the act of dispensing the indicating compound with the planarizing solution comprises adding the fluorescent material to the planarizing solution.

* * * * *